(12) United States Patent
Liviero et al.

(10) Patent No.: US 6,335,368 B1
(45) Date of Patent: Jan. 1, 2002

(54) USE OF ALVERINE FOR REDUCING WRINKLES

(75) Inventors: Christel Liviero, Paris; Lionel Breton, Versailles; Nathalie Pineau, Poitiers, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/666,343

(22) Filed: Sep. 21, 2000

(30) Foreign Application Priority Data

Sep. 21, 1999 (FR) .................................................. 99 11772

(51) Int. Cl.⁷ ......................... A61K 31/195; A61K 31/19; A61K 31/135
(52) U.S. Cl. ........................... 514/561; 514/574; 514/649
(58) Field of Search ................................... 514/561, 574, 514/649

(56) References Cited

U.S. PATENT DOCUMENTS 4,510,145 A * 4/1985 Schacher ...................... 514/415
5,719,197 A * 2/1998 Kanios et al. ............. 514/772.6

FOREIGN PATENT DOCUMENTS

| GB | 2 218 633 A | 11/1989 |
| WO | 83/03755 | 11/1983 |

OTHER PUBLICATIONS

Patent Abstracts of Japan, vol. 12, No. 117, Apr. 13, 1988, Abstract of JP 62 240628 A.

* cited by examiner

Primary Examiner—Raymond Henley, III
(74) Attorney, Agent, or Firm—Burns, Doane, Swecker & Mathis, L.L.P.

(57) ABSTRACT

The present invention relates to the use of at least an effective amount of Alverine or a salt thereof in a composition or for the preparation of a composition, the Alverine or a salt thereof or the composition being intended to decontract and/or relax skin tissue and/or subcutaneous tissue, in particular in order to reduce the wrinkles and fine lines of the skin.

36 Claims, No Drawings

USE OF ALVERINE FOR REDUCING WRINKLES

This application claims priority under 35 U.S.C. §§119 and/or 365 to Application No. 9911772 filed in France on Sep. 21, 1999; the entire content of which is hereby incorporated by reference.

The present invention relates to the use of at least an effective amount of Alverine or a salt thereof in a composition or for the preparation of a composition, the Alverine or a salt thereof or the composition being intended to decontract and/or relax skin tissue and/or subcutaneous tissue, in particular in order to reduce the wrinkles and fine lines of the skin.

Women, and even men, nowadays tend to wish to look young for as long as possible and consequently seek to fade out the marks of ageing of the skin, which are reflected in particular by wrinkles and fine lines. In this respect, advertisement and the fashion world mention products intended to maintain, for as long as possible, a radiant skin free of wrinkles, which are signs of a youthful skin, and all the more so since physical appearance has an influence on the psyche and/or the morale. It is important to feel physically and psychologically young.

Hitherto, wrinkles and fine lines were reduced using cosmetic products containing active agents that act on the skin, for example by moisturizing it or by improving its cell renewal or alternatively by promoting the synthesis of collagen, of which skin tissue is composed. However, it is not known at the present time how to treat wrinkles by acting on the muscular components present in the skin. The present invention lies in this approach.

It is known that the skin muscles of the face are under the control of motor nerve afferences of the facial nerve and that, moreover, the interlobular septa of the hypoderm contain fibers which constitute a striated muscle tissue (panniculus carnosus). Moreover, it is also known that a sub-population of dermal fibroblasts, known as myofibroblasts, has characteristics in common with muscle tissue.

The Applicant has in particular observed, in certain pathological and therapeutic situations, the role played on the facial wrinkles by the nerves controlling this assembly of muscle tissue. Thus, in attacks of the facial nerve, in which the transmission of the nerve influx is interrupted and/or diminished, the innervation region reveals paralysis of facial muscles. This facial paralysis is reflected, among other clinical signs, by an attenuation or even a disappearance of wrinkles.

Conversely, in states of muscular hypercontraction of the face, the Applicant has observed an increase in facial wrinkles. Furthermore, it has also observed an increase in facial wrinkles in the muscular hypertonic states of Parkinson's disease and side effects induced by neuroleptic agents.

Moreover, it has been shown that botulinum toxin, which was originally used to reduce spasms, can act on muscle spasticity conditions (see A. Blitzer et al., Arch. Otolaryngol. Head Neck Surg., 1993, 119, pages 1018 to 1022) and on the wrinkles of the glabella, which are the wrinkles between the eyebrows (see J. D. Carruters et al., J. Dermatol. Surg. Oncol., 1992, 18, pages 17 to 21). This botulinum toxin is moreover conventionally used in plastic surgery in the treatment of wrinkles. Consequently, it is possible to act with a pharmacological action on the neuromuscular component of wrinkles.

After numerous tests, the Applicant has been able to determine that contractile muscle fibers, and in particular striated muscle fibers, which are under the direct control of the neuromuscular influx, play an essential role in the formation of wrinkles and that modulating the neuromuscular influx attenuates not only wrinkles but also fine lines and also has a "smoothing" effect on the skin microrelief.

Physiologically, the activity of striated muscles (with the exception of the cardiomyocyte) is triggered by the nervous system, and the activity of smooth muscles is spontaneous and modulated by various stimuli of hormonal or nervous type.

The cells which are the cause of spontaneous contractions are the "pacemaker" cells: the propagation of the electrical excitation wave takes place little by little in the zone of least electrical resistance of the cell membranes.

Outside of spontaneous activity, the excitation of smooth muscle fibers can be triggered by various stimuli: mechanical stretching, the presence of neurotransmitters or intestinal hormones acting specifically on certain cell receptors, certain agents having an agonist or antagonist effect on these same receptors.

Irrespective of the type of fibre (smooth or striated), the common final messenger which is the cause of the contraction is the calcium ion ($Ca^{2+}$).

However, the intervention of this cation in the contractile mechanism is entirely different depending on the type of fiber (smooth or striated).

The studies by the Ebashi group have shown that, in smooth muscles (unlike striated muscles), the sliding of the actin and myosin molecules does not take place after the inhibition exerted by troponin has been lifted with $Ca^{2+}$. The cation exerts a direct activating effect on the actin-myosin linkage in combination with a protein known as leiotonin C. The joint action of $Ca^{2+}$ and leiotonin C is responsible for the phosphorylation of the light chains of myosin which causes the contraction.

Furthermore, the relaxation of smooth muscles is very active, unlike that of striated muscle. It is dependent on hormonal and nervous mediators.

The demonstration of these physiological activities is at the origin of the control of the digestive motility by pharmacological agents.

Thus, Alverine or di(phenylpropyl)ethylamine, also known as Spasmaverine or Diproline, is known as a digestive smooth muscle relaxant.

The Applicant has now discovered that the relaxing effect of Alverine is not specific for smooth muscle.

Alverine can induce a decontracting and/or relaxing effect on striated muscle and thus, consequently, can constitute an active agent that is advantageous for correcting wrinkles and/or fine lines and for promoting smooth skin.

To the Applicant's knowledge, such a property is not described or suggested anywhere in the prior art.

The present invention thus relates to the use in a composition or for the preparation of a composition, of at least an effective amount of Alverine or of a salt thereof, the Alverine or the salt thereof or the composition being intended to relax and/or decontract the skin tissue and/or subcutaneous tissue.

According to the invention, the expression "Alverine salts" means the organic or inorganic salts of Alverine.

As organic salts which can be used according to the invention, mention may be made of Alverine gluconate, Alverine acetate, Alverine citrate, Alverine oleate and Alverine oxalate.

Inorganic Alverine salts which may be mentioned are mineral salts such as Alverine chloride, Alverine borate, Alverine nitrate, Alverine phosphate, Alverine sulphate and Alverine carbonate.

It is thus understood that in the text, except where otherwise indicated, the use of the term "Alverine" should be understood as meaning Alverine both in ionic form and in the form of salts.

Preferably, according to the invention, the organic salt is Alverine citrate and the inorganic salt is Alverine chloride.

This use is found to be particularly effective for reducing wrinkles and/or fine lines and/or for making the skin smooth.

Thus, a subject of the invention is also the use of at least an effective amount of Alverine or of a salt thereof in a composition or for the preparation of a composition, the Alverine or a salt thereof or the composition being intended for reducing wrinkles and/or fine lines.

More particularly, the relaxation and/or decontraction of the skin tissue and/or subcutaneous tissue is a muscular decontraction or relaxation.

The use of Alverine according to the invention can be preventive and/or curative.

A subject of the invention is also a composition intended for relaxing and/or decontracting skin tissue and/or subcutaneous tissue, comprising at least an effective amount of Alverine or a salt thereof.

A subject of the invention is also a composition intended for reducing wrinkles and fine lines and/or for smoothing the skin, comprising at least an effective amount of Alverine or a salt thereof.

According to the invention, the composition is intended for cosmetic or dermatological use, preferably cosmetic use.

According to the invention, the composition comprising Alverine or a salt thereof can be applied either locally, i.e. topically, or by subcutaneous and/or intradermal injection, or systemically or generally, i.e. orally and/or by intramuscular injection.

The composition containing Alverine or a salt thereof is preferably applied topically.

The composition of the invention, intended for topical application, contains a physiologically acceptable medium, i.e. a medium which is compatible with the skin, including the scalp, mucous membranes and/or the eyes. The composition can in particular constitute a cosmetic or dermatological composition.

A subject of the invention is also a cosmetic treatment process for reducing wrinkles and/or fine lines, comprising the administration of a composition comprising at least an effective amount of Alverine or a salt thereof.

According to the invention, the term "administration" means topical application, injection or ingestion.

According to the invention, the cosmetic treatment process preferably comprises a topical application.

The amount of Alverine or a salt thereof which can be used according to the invention obviously depends on the desired effect.

By way of example, the weight amount of Alverine or a salt thereof which-can be used according to the invention can be, for example, between 0.0001% and 20% and preferably between 0.001% and 5% relative to the total weight of the composition.

The compositions according to the invention can be in any pharmaceutical form normally used for topical, injection or oral application.

The compositions according to the invention are preferably in a pharmaceutical form used for topical application.

The amounts of the various constituents in the compositions according to the invention are those conventionally used in the fields under consideration and are appropriate to their pharmaceutical form.

For topical application, the compositions of the invention comprise a medium which is compatible with the skin. These compositions can be, in particular, in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These pharmaceutical forms are prepared according to the usual methods of the fields under consideration.

These compositions for topical application can in particular constitute a cosmetic or dermatological protective, treatment or care composition for the face, for the neck, for the hands or for the body (for example day creams, night creams, antisun oils or creams, and body milks), a make-up composition (for example a foundation) or an artificial tanning composition.

When the composition of the invention is an emulsion, the proportion of fatty substances contained therein can range from 5% to 80% by weight, and preferably from 5% to 50% by weight, relative to the total weight of the composition. The fatty substances and emulsifiers used in the composition in emulsion form are chosen from those conventionally used in cosmetics or dermatology.

As fatty substances which can be used in the invention, mention may be made of mineral oils (petroleum jelly), plant oils (liquid fraction of karite butter) and hydrogenated derivatives thereof, animal oils, synthetic oils (perhydrosqualene), silicone oils (polydimethylsiloxane) and fluoro oils. Other fatty substances which may also be mentioned are fatty alcohols (cetyl alcohol, stearyl alcohol), fatty acids (stearic acid) and waxes.

The emulsifiers can be present in the composition in a proportion ranging from 0.3% to 50% by weight, and preferably from 0.5% to 30% by weight, relative to the total weight of the composition.

In a known manner, the cosmetic or dermatological compositions of the invention can also contain adjuvants that are common in the corresponding fields, such as hydrophilic or lipophilic gelling agents, preserving agents, antioxidants, solvents, fragrances, fillers, screening agents and dyestuffs. Moreover, these compositions can contain hydrophilic or lipophilic active agents. The amounts of these various adjuvants or active agents are those conventionally used in cosmetics or dermatology, and, for example, from 0.01% to 20% relative to the total weight of the composition. Depending on their nature, these adjuvants or active agents can be introduced into the fatty phase, into the aqueous phase and/or into the lipid vesicles.

Among the active agents which can contain the compositions of the invention, mention may be made in particular of other active agents having an effect on the treatment of wrinkles or fine lines, and in particular keratolytic active agents. The term "keratolytic" means an active agent which has desquamating, exfoliating or erasing properties, or an active agent capable of softening the horny layer.

Among the active agents having an effect on the treatment of wrinkles or fine lines and which may be contained by the compositions of the invention, mention may be made in particular of hydroxy acids and retinoids.

The hydroxy acids can be, for example, α-hydroxy acids or β-hydroxy acids, which may be linear, branched or cyclic, and saturated or unsaturated. The hydrogen atoms of the carbon-based chain can, in addition, be substituted with halogens, halogenated, alkyl, acyl, acyloxy, alkoxycarbonyl or alkoxy radicals containing from 2 to 18 carbon atoms.

The hydroxy acids which can be used are, in particular, glycolic acid, lactic acid, malic acid, tartaric acid, citric acid, 2-hydroxyalkanoic acids, mandelic acid and salicylic acid, as well as alkyl derivatives thereof such as 5-n-octanoylsalicylic acid, 5-n-dodecanoylsalicylic acid, 5-n-decanoylsalicylic acid, 5-n-octylsalicylic acid, 5-n-heptyloxysalicylic acid or 4-n-heptyloxysalicylic acid, 2-hydroxy-3-methylbenzoic acid, or alkoxy derivatives thereof such as 2-hydroxy-3-methoxybenzoic acid.

The retinoids may be, in particular, retinoic acid (all-trans or 13-cis) and derivatives thereof, retinol (vitamin A) and esters thereof such as retinyl palmitate, retinyl acetate and retinyl propionate, as well as salts thereof.

These active agents can be used in particular at concentrations ranging from 0.0001% to 5% by weight relative to the total weight of the composition.

When the compositions of the invention are intended for oral application, they can be in the usual pharmaceutical forms in this field, such as tablets, gel capsules, drinkable products, in particular those made up at the time of use, granules or powders, in the usual excipients for such an application.

When the compositions of the invention are intended to be injected, they can be in the form of solutions containing the excipients usually used for injections, and, for example, in the form of an isotonic sodium chloride solution.

The examples and compositions below illustrate the invention without limiting it in any way. In the compositions, the proportions indicated are percentages by weight, except where otherwise mentioned.

EXAMPLE 1

Activity of Alverine in a model of nerve/muscle junction (motor plate) measured in a preparation of phrenic nerve/diaphragm isolated from rat (striated muscle) (Pollard B. J. et al, Br. J. Anaesth., 1988, 61, 419–424).

The phrenic nerve and the diaphragm are carefully isolated and placed in a 50 ml tank filled with survival fluid (Krebs-Henseleit fluid) maintained at a temperature of 37° C. and oxygenated using an oxygen/$CO_2$ mixture (95/5).

The variations in tension of the diaphragm are recorded with an initial preload of several grams.

After a relaxation period of 30 min., the diaphragm is stimulated indirectly via the phrenic nerve.

On each preparation, the effect of the test products was evaluated in a first stage as regards the contractions induced by indirect stimulation via stimulation of the phrenic nerve (0.1 to 0.5 volts, 0.3 ms, 0.1 Hz) at increasing and cumulative concentrations from $10^{-9}$ M to $10^{-4}$ M.

In the event of an effect at the end of the test, the diaphragm is stimulated directly in order to determine whether or not the inhibition of the neurotransmission results from a pre-junctional blockage or a post-junctional blockage.

The results obtained in the motor plate model with Alverine are given in the table below:

| % of inhibition | $10^{-4}$ M Alverine | |
|---|---|---|
| | 1st study | 2nd study |
| Indirect stimulation | 100 | 100 |
| Direct stimulation | 61.4 | 42.2 |

At a concentration of $10^{-4}$ M, Alverine completely inhibits the contractions induced by the indirect stimulations and inhibits a proportion of about 50% of those induced by the direct stimulations. In conclusion, Alverine preferentially intervenes on the neuromuscular junction by modifying the calcium exchanges, which also explains its direct-stimulation effect.

EXAMPLE 2

Examples of compositions according to the invention.

| Composition 1: Care lotion for the face | |
|---|---|
| Alverine | 1.00% |
| Antioxidant | 0.05% |
| Preserving agent | 0.30% |
| Ethanol (solvent) | 8.00% |
| Water | qs 100% |

The lotion obtained acts on wrinkles in the course of repeated use (application twice-daily for one month).

| Composition 2: Care gel for the face | |
|---|---|
| Alverine | 2.00% |
| Hydroxypropylcellulose* | 1.00% |
| Preserving agent | 0.30% |
| Ethanol (solvent) | 15.00% |
| Antioxidant | 0.05% |
| Water | qs 100% |

*Klucel H ® sold by the company Hercules (gelling agent).

The gel obtained acts on wrinkles. It can be applied daily, morning and evening, for one month.

| Composition 3: Care cream for the face (oil-in-water emulsion) | |
|---|---|
| Alverine | 0.50% |
| Glyceryl stearate | 2.00% |
| Polysorbate-60** | 1.00% |
| Stearic acid | 1.40% |
| Triethanolamine | 0.70% |
| Carbomer*** | 0.40% |
| Liquid fraction of karite butter | 12.00% |
| Perhydrosqualene | 12.00% |
| Preserving agent | 0.30% |
| Fragrance | 0.50% |
| Antioxidant | 0.05% |
| Water | *qs 100% |

**Tween 60 ® sold by the company ICI;
***Carbopol 940 ® sold by the company Goodrich An unctuous white cream which acts on wrinkles and fine lines and which can be applied daily is obtained.

| Composition 4: Care cream for the face (oil-in-water emulsion) | |
|---|---|
| Alverine | 5.00% |
| Glyceryl mono-, distearate | 2.00% |
| Cetyl alcohol | 1.50% |
| Cetylstearyl alcohol/33 EO oxyethylenated cetylstearyl alcohol mixture | 7.00% |
| Polydimethylsiloxane | 1.50% |
| Liquid petroleum jelly | 17.50% |
| Preserving agent | 0.30% |
| Fragrance | 0.50% |
| Glycerol | 12.50% |
| Water | qs 100% |

We claim:
1. Cosmetic treatment process for reducing wrinkles and/or fine lines, comprising the administration of a composition comprising at least an effective amount of Alverine or a salt thereof.

2. A process for relaxing and/or decontracting a skin tissue and/or subcutaneous tissue comprising administering a skin or subcutaneous tissue relaxing and/or decontracting effective amount of Alverine, an Alverine salt or a composition comprising Alverine or an Alverine salt to a subject in need of relaxation or decontraction of the skin tissue and/or subcutaneous tissue.

3. A process for smoothing skin comprising administering Alverine, an Alverine salt or a composition comprising Alverine or an Alverine salt to a subject in need of skin smoothing.

4. The process of claim 1, wherein said composition comprises between 0.0001% and 10% by weight of Alverine or the Alverine salt.

5. The process of claim 2, wherein said composition comprises between 0.0001% and 10% by weight of Alverine or the Alverine salt.

6. The process of claim 3, wherein said composition comprises between 0.0001% and 10% by weight of Alverine or the Alverine salt.

7. The process of claim 4, wherein said composition comprises between 0.001% and 5% by weight of Alverine or the Alverine salt.

8. The process of claim 5, wherein said composition comprises between 0.001% and 5% by weight of Alverine or the Alverine salt.

9. The process of claim 6, wherein said composition comprises between 0.001% and 5% by weight of Alverine or the Alverine salt.

10. The process of claim 1, wherein said Alverine salt is an organic or inorganic salt.

11. The process of claim 2, wherein said Alverine salt is an organic or inorganic salt.

12. The process of claim 3, wherein said Alverine salt is an organic or inorganic salt.

13. The process of claim 10, wherein the organic salt is Alverine gluconate, Alverine acetate, Alverine citrate, Alverine oleate or Alverine oxalate.

14. The process of claim 11, wherein the organic salt is Alverine gluconate, Alverine acetate, Alverine citrate, Alverine oleate or Alverine oxalate.

15. The process of claim 12, wherein the organic salt is Alverine gluconate, Alverine acetate, Alverine citrate, Alverine oleate or Alverine oxalate.

16. The process of claim 13, wherein the organic salt is Alverine citrate.

17. The process of claim 14, wherein the organic salt is Alverine citrate.

18. The process of claim 15, wherein the organic salt is Alverine citrate.

19. The process of claim 10, wherein the inorganic salt is Alverine chloride, Alverine borate, Alverine nitrate, Alverine phosphate, Alverine sulfate or Alverine carbonate.

20. The process of claim 11, wherein the inorganic salt is Alverine chloride, Alverine borate, Alverine nitrate, Alverine phosphate, Alverine sulfate or Alverine carbonate.

21. The process of claim 12, wherein the inorganic salt is Alverine chloride, Alverine borate, Alverine nitrate, Alverine phosphate, Alverine sulfate or Alverine carbonate.

22. The process of claim 19, wherein the inorganic salt is Alverine chloride.

23. The process of claim 20, wherein the inorganic salt is Alverine chloride.

24. The process of claim 21, wherein the inorganic salt is Alverine chloride.

25. A process for relaxing and/or decontracting striated muscle of a skin tissue and/or subcutaneous tissue comprising administering a skin or subcutaneous striated muscle relaxing and/or decontracting effective amount of Alverine, an Alverine salt or a composition comprising Alverine or an Alverine salt to a subject in need of relaxation and/or decontraction of striated muscle of the skin tissue and/or subcutaneous tissue.

26. The process of claim 25, wherein said composition comprises between 0.0001% and 10% by weight of Alverine or the Alverine salt.

27. The process of claim 26, wherein said composition comprises between 0.001% and 5% by weight of Alverine or the Alverine salt.

28. The process of claim 25, wherein said Alverine salt is an organic or inorganic salt.

29. The process of claim 28, wherein the organic salt is Alverine gluconate, Alverine acetate, Alverine citrate, Alverine oleate or Alverine oxalate.

30. The process of claim 29, wherein the organic salt is Alverine citrate.

31. The process of claim 25, wherein the inorganic salt is Alverine chloride, Alverine borate, Alverine nitrate, Alverine phosphate, Alverine sulfate or Alverine carbonate.

32. The process of claim 31, wherein the inorganic salt is Alverine chloride.

33. The process of claim 1, wherein Alverine, the Alverine salt or said composition is administered topically.

34. The process of claim 2, wherein Alverine, the Alverine salt or said composition is administered topically.

35. The process of claim 3, wherein Alverine, the Alverine salt or said composition is administered topically.

36. The process of claim 25, wherein Alverine, the Alverine salt or said composition is administered topically.

* * * * *